United States Patent
Li et al.

(10) Patent No.: US 6,399,838 B1
(45) Date of Patent: Jun. 4, 2002

(54) PROCESS FOR PREPARING 2,6-DIMETHYLPHENOL

(75) Inventors: Kuo-Tseng Li, Taichung; Pang Yih Liu, Hsinchu, both of (TW)

(73) Assignee: National Science Council (TW)

(*) Notice: Subject to any disclaimer, the term of this patent is extended or adjusted under 35 U.S.C. 154(b) by 0 days.

(21) Appl. No.: 09/775,764

(22) Filed: Feb. 2, 2001

(30) Foreign Application Priority Data

Nov. 17, 2000 (TW) ........................................ 89124403 A

(51) Int. Cl.[7] .............................................. C07C 37/00
(52) U.S. Cl. ........................ 568/802; 568/432; 568/805; 568/806
(58) Field of Search ................................ 568/432, 802, 568/806, 805

(56) References Cited

U.S. PATENT DOCUMENTS

| | | | |
|---|---|---|---|
| 4,533,767 A | 8/1985 | Talley | 568/805 |
| 4,533,768 A | 8/1985 | Talley | 568/805 |
| 4,560,810 A | 12/1985 | Talley et al. | 568/805 |
| 4,929,766 A | 5/1990 | Schnatterer et al. | 568/432 |
| 5,475,156 A | 12/1995 | Caruso et al. | 568/780 |

FOREIGN PATENT DOCUMENTS

JP 62-240642 A * 10/1987

OTHER PUBLICATIONS

Goldstein, J. Org. Chem., vol. 49, pp. 1613–1620 (1984).*

* cited by examiner

*Primary Examiner*—Michael L. Shippen

(57) ABSTRACT

A process for preparing 2,6-dimethylphenol from 2,4,6-trimethylphenol is provided. The process includes two steps: (1) selective oxidation of 2,4,6-trimethylphenol to 3,5-dimethyl-4-hydroxybenzaldehyde and (2) deformylation of the resulting benzaldehyde to 2,6-dimethylphenol. In step (1), the 2,4,6-trimethylphenol is reacted with oxygen-containing gases at temperatures of 20 to 200° C. in the presence of an iron-containing catalyst, which has higher 3,5-dimethyl-4-hydroxybenzaldehyde selectivity than the known copper-based catalysts. In step (2), a copper-containing catalyst is used to replace the customarily used precious metal catalysts for the effective deformylation of the 3,5-dimethyl-4-hydroxybenzaldehyde to 2,6-dimethylphenol.

15 Claims, No Drawings

PROCESS FOR PREPARING 2,6-DIMETHYLPHENOL

FIELD OF THE INVENTION

The present invention relates to a process for preparing 2,6-dimethylphenol, and more particularly to a process for preparing 2,6-dimethylphenol from 2,4,6-trimethylphenol.

BACKGROUND OF THE INVENTION

Poly(2,6-dimethyl-1,4-phenylene oxide), abbreviated as PPO, is one of the leading engineering polymers. PPO blends with polystyrene or polyamide (known as modified PPO or MPPO) are widely used in the formation of cases of personal computers or their peripheral equipment, the parts used in vehicles, electronic or electrical equipment, and house or office appliances.

2,6-dimethylphenol is the starting material for the manufacture of PPO. Typical industrial processes for preparing 2,6-dimethylphenol involve the reaction of phenol and methanol in the presence of a metal oxide catalyst. The major by-product of this reaction is 2,4,6-trimethylphenol, which has little practical use. It is desirable to convert 2,4,6-trimethylphenol into 2,6-dimethylphenol to improve the process economic benefit. The known methods for converting 2,4,6-trimethylphenol into 2,6-dimethylphenol include a catalytic dealkylation process and a catalytic hydrodealkylation process to remove the methyl group in the $4^{th}$ position of 2,4,6-trimethylphenol (described in U.S. Pat. Nos. 4,533,767, 4,533,768, 4,560,810 and 4,929,766 ). However, the 2,6-dimethylphenol selectivities obtained from these dealkylation methods are rather low.

Another method for the converting of 2,4,6-trimethylphenol to 2,6-dimethylphenol is disclosed in U.S. Pat. No. 5,475,156. The process comprises the selective oxidation of 2,4,6-trimethylphenol to 3,5-dimethyl-4-hydroxybenzaldehyde in the presence of a copper-based catalyst, and the deformylation of the resulting 3,5-dimethyl-4-hydroxybenzaldehyde to 2,6-dimethylphenol in the presence of a palladium catalyst. However, the process has the following disadvantages: (1) significant amounts of undesirable by-product, 2,6-dimethyl-p-benzoquinone, are produced from the selective oxidation catalyzed by the copper-based catalysts, (2) the palladium catalyst used for catalyzing the deformylation reaction is very expensive.

The present invention provides an improved process for preparing 2,6-dimethylphenol to overcome the problems described above.

SUMMARY OF THE INVENTION

It is an object of the present invention to provide a process for preparing 2,6-dimethylphenol from 2,4,6-trimethylphenol.

In accordance with one aspect of the present invention, the process for preparing 2,6-dimethylphenol from a 2,4,6-trimethylphenol solution includes steps of (1) effecting a selective oxidation of the 2,4,6-trimethylphenol solution by reacting with an oxygen-containing gas to produce 3,5-dimethyl-4-hydroxybenzaldehyde at temperatures of 20 to 200° C. in the presence of an iron-containing catalyst system and a first solvent, and (2) effecting a deformylation of the 3,5-dimethyl-4-hydroxybenzaldehyde to 2,6-dimethylphenol at temperatures of 50 to 400° C. in the presence of a copper-containing catalyst system and a second solvent.

Preferably, the first solvent used for the selective oxidation is an alcohol having 1 to 6 carbon atoms. More preferably, the first solvent is methanol.

Preferably, the iron-containing catalyst system used for the selective oxidation includes an iron-containing material and a carrier. The iron-containing material is preferably one selected from a group consisting of iron halide, iron oxide, iron sulfide, iron sulfate, iron carbonate, iron hydroxide, iron complex, iron ion, iron metal, organic iron compound and the combination thereof. More preferably, the iron-containing material is iron halide. Much more preferably, the iron-containing material is iron chloride. The carrier of the iron-containing catalyst system is used for supporting the iron-containing material and selected from a group consisting of alumina, silica, titanium dioxide, zirconium dioxide, alumina-silica and zeolite.

Preferably, the iron-containing catalyst system further includes a nitrogen-containing organic compound as promoter. The nitrogen-containing organic compound is preferably an oxime, and more preferably an acetone oxime.

Preferably, the second solvent used for the deformylation is an alkane having 10 to 20 carbon atoms.

Preferably, the copper-containing catalyst system used for the deformylation includes a copper-containing material and a carrier. The copper-containing material is preferably one selected from a group consisting of copper halide, copper oxide, copper sulfide, copper sulfate, copper lactate, copper hydroxide, copper nitrate, copper oleate, copper phosphate, copper phosphoric, copper complex, copper ion, copper metal, organic copper compound and the combination thereof. More preferably, the copper-containing material is copper halide. The carrier of the copper-containing catalyst system is used for supporting the copper-containing material and selected from a group consisting of alumina, silica, titanium dioxide, zirconium dioxide, alumina-silica and zeolite.

It is another object of the present invention to provide a process for improving the selectivity of 3,5-dimethyl-4-hydroxybenzaldehyde from a 2,4,6-trimethylphenol solution. The process is carried out by reacting a the 2,4,6-trimethylphenol solution with an oxygen-containing gas to produce 3,5-dimethyl-4-hydroxybenzaldehyde at temperatures of 20 to 200° C. in the presence of an iron-containing catalyst system and a solvent.

It is another object of the present invention to provide a process for preparing 2,6-dimethylphenol form 3,5-dimethyl-4-hydroxybenzaldehyde by using a cheaper catalyst in place of the palladium catalyst. The process is carried out by performing a deformylation of the 3,5-dimethyl-4-hydroxybenzaldehyde to the 2,6-dimethylphenol at temperatures of 50 to 400° C. in the presence of a copper-containing catalyst system and a solvent.

The above objects and advantages of the present invention will become more readily apparent to those ordinarily skilled in the art after reviewing the following detailed description, in which:

DETAILED DESCRIPTION OF THE PREFERRED EMBODIMENTS

EXAMPLE 1

Selective Oxidation of 2,4,6-trimethylphenol in the Presence of an Iron-containing Catalyst 60 ml of methanol (available from Fisher Chemical Co.), 8.16 g of 2,4,6-trimethylphenol (available from Lancaster Co.) and 0.49 g of iron(II) chloride, $FeCl_2.nH_2O$ (available from Showa Chemical Co.) are mixed and introduced into a glass vessel. In this example, the molar ratio of 2,4,6- trimethylphenol to iron is 20:1. Subsequently, the glass vessel is placed in a 300 ml batch-type reactor (manufactured by PAAR Co.) equipped with a stirrer. The reactor is heated to a predetermined temperature, e.g. 70 or 90° C., and under a predetermined pressure, e.g. 10 atm, of oxygen to effect the selective oxidation for a period. The reaction product is taken out at different time intervals and then subjected to a gas chromatographic separation to analyze the components.

The results are shown in Table 1, wherein the conversion of 2,4,6-trimethylphenol is defined as the moles of 2,4,6-trimethylphenol reacted per moles of 2,4,6-trimethylphenol fed, the selectivity of 3,5-dimethyl-4-hydroxybenzaldehyde is defined as the moles of 3,5-dimethyl-4-hydroxybenzaldehyde produced per moles of 2,4,6-trimethylphenol reacted, and the selectivity of 2,6-dimethyl-p-benzoquinone is defined as the moles of 2,6-dimethyl-p-benzoquinone produced per moles of 2,4,6-trimethylphenol reacted.

TABLE 1

Catalytic performance of iron(II) chloride catalyst for the selective oxidation of 2,4,6-trimethylphenol

| Temperature (° C.) | Reaction time (Hr) | Conversion of 2,4,6-trimethylphenol (%) | Selectivity of 3,5-dimethyl-4-hydroxybenzaldehyde (%) | Selectivity of 2,6-dimethyl-p-benzoquinone (%) |
|---|---|---|---|---|
| 90 | 8 | 92.7 | 80.0 | 8 |
| 70 | 10 | 90.4 | 82.3 | 3.7 |

The result in Table 1 shows that only a small amount of 2,6-dimethyl-p-benzoquinone (its selectivity<10%) is produced when the conversion of 2,4,6-trimethylphenol is about 90%.

Comparative Example 1

Selective Oxidation of 2,4,6-trimethylphenol in the Presence of a Copper-containing Catalyst The procedure and the materials are the same as those mentioned in example 1, except that the iron(II) chloride catalyst is replaced by copper chloride, $CuCl_2 \cdot nH_2O$. The results are shown in Table 2.

TABLE 2

Catalytic performance of copper chloride catalyst for the selective oxidation of 2,4,6-trimethylphenol

| Temperature (° C.) | Reaction time (Hr) | Conversion of 2,4,6-trimethylphenol (%) | Selectivity of 3,5-dimethyl-4-hydroxybenzaldehyde (%) | Selectivity of 2,6-dimethyl-p-benzoquinone (%) |
|---|---|---|---|---|
| 90 | 1.7 | 92.6 | 58.7 | 19.5 |
| 70 | 2.7 | 93.8 | 64.4 | 15.5 |

From the results shown in Table 1 and Table 2, it is apparent that the iron-containing catalyst has higher selectivity of 3,5-dimethyl-4-hydroxybenzaldehyde and much less selectivity of 2,6-dimethyl-p-benzoquinone than the copper-containing catalyst at the same conversion level of 2,4,6-trimethylphenol. Thus, the iron-containing catalyst according to the present invention has better catalytic performance than the copper-containing catalyst used in the prior art.

EXAMPLE 2

Catalytic Performance of the Iron-containing Catalyst with the Addition of Oxime The procedure and the materials are the same as those mentioned in example 1, except that 0.219 g of acetone oxime is further added. The results are shown in Table 3 at the reaction temperature of 70° C.

TABLE 3

Effect of the addition of acetone oxime on the catalytic performance of iron(II) chloride catalyst for the selective oxidation of 2,4,6-trimethylphenol at 70° C.

| additive | Reaction time (Hr) | Conversion of 2,4,6-trimethylphenol (%) | Selectivity of 3,5-dimethyl-4-hydroxybenzaldehyde (%) | Selectivity of 2,6-dimethyl-p-benzoquinone (%) |
|---|---|---|---|---|
| None | 10 | 90.4 | 82.3 | 3.7 |
| Acetone oxime | 1.67 | 97.0 | 76.7 | 2.5 |

The results in Table 3 show that the addition of acetone oxime increases the activity of iron-containing catalyst for the selective oxidation of 2,4,6-trimethylphenol. At the temperature of 70° C., the conversion of 2,4,6-trimethylphenol is 90.4% at 10 hours of reaction without the addition of acetone oxime. However, the conversion of 2,4,6-trimethylphenol reaches 97% for only a period of 1.67 hours with the addition of acetone oxime.

EXAMPLE 3

Deformylation of 3,5-dimethyl-4-hydroxybenzaldehyde to 2,6-dimethylphenol in the Presence of a Copper-containing Catalyst 10 ml of tetradecane (available from Lancaster Co.) is introduced into a 15 ml of glass vessel equipped with a magnetic stirrer. Nitrogen gas is introduced to purge the glass vessel so as to remove oxygen gas. Subsequently, the glass vessel is heated to a predetermined temperature, e.g. 225 or 250° C., and 0.5 g of 3,5-dimethyl-4-hydroxybenzaldehyde (available from Lancaster Co.) and 0.41 mg of copper chloride, $CuCl_2 \cdot nH_2O$, (available from Showa Chemical Co.) are added to effect the deformylation reaction for a period. The reaction product is taken out at different time intervals and then subjected to a gas chromotographic separation to analyze the components.

The results are shown in Table 4, wherein the conversion of 3,5-dimethyl-4-hydroxybenzaldehyde is defined as the moles of 3,5-dimethyl-4-hydroxybenzaldehyde reacted per moles of 3,5-dimethyl-4-hydroxybenzaldehyde fed, and the selectivity of 2,6-dimethylphenol is defined as the moles of 2,6-dimethylphenol produced per moles of 3,5-dimethyl-4-hydroxybenzaldehyde reacted.

TABLE 4

Catalytic performance of copper chloride catalyst for the deformylation of 3,5-dimethyl-4-hydroxybenzaldehyde

| Temperature (° C.) | Reaction time (Hr) | Conversion of 3,5-dimethyl-4-hydroxybenzaldehyde (%) | Selectivity of 2,6-dimethylphenol (%) |
|---|---|---|---|
| 250 | 6 | 58.3 | 94 |
| 225 | 10 | 66.4 | 97.7 |

The results in Table 4 show that the copper containing catalyst can effectively catalyze the deformylation of 3,5-dimethyl-4-hydroxybenzaldehyde to produce 2,6-dimethylphenol. Thus, the customarily used palladium catalyst can be replaced by a cheaper copper-containing catalyst.

Certainly, the iron-containing catalyst used in the selective oxidation of 2,4,6-trimethylphenol is not limited but includes iron halide, iron oxide, iron sulfide, iron sulfate, iron carbonate, iron hydroxide, iron complex, iron ion, iron metal, organic iron compound and the combination thereof. Furthermore, the iron-containing catalyst is supported on a carrier selected from a group consisting of alumina, silica, titanium dioxide, zirconium dioxide, alumina-silica and zeolite.

Certainly, the copper-containing catalyst used in the deformylation of 3,5-dimethyl-4-hydroxybenzaldehyde to 2,6-dimethylphenol is not limited but includes copper halide, copper oxide, copper sulfide, copper sulfate, copper lactate, copper hydroxide, copper nitrate, copper oleate, copper phosphate, copper phosphoric, copper complex, copper ion, copper metal, organic copper compound and the combination thereof. Furthermore, the copper-containing catalyst is supported on a carrier selected from a group consisting of alumina, silica, titanium dioxide, zirconium dioxide, alumina-silica and zeolite.

The process for preparing 2,6-dimethylphenol from 2,4,6-trimethylphenol has the advantages of increasing the selectivity of 3,5-dimethyl-4-hydroxybenzaldehyde and reducing the production of 2,6-dimethyl-p-benzoquinone in the selective oxidation of 2,4,6-trimethylphenol, and replacing the precious metal catalyst for the effective deformylation of the 3,5-dimethyl-4-hydroxybenzaldehyde to 2,6-dimethylphenol.

While the invention has been described in terms of what are presently considered to be the most practical and preferred embodiments, it is to be understood that the invention needs not be limited to the disclosed embodiment. On the contrary, it is intended to cover various modifications and similar arrangements included within the spirit and scope of the following claims which are to be accorded with the broadest interpretation so as to encompass all such modifications and similar structure.

What is claimed is:

1. A process for preparing 2,6-dimethylphenol from a 2,4,6-trimethylphenol solution, comprising steps of:
    effecting a selective oxidation of said 2,4,6-trimethylphenol solution by reacting with an oxygen-containing gas to produce a 3,5-dimethyl-4-hydroxybenzaldehyde at temperatures of 20 to 200° C. in the presence of an iron-containing catalyst system and a first solvent; and
    effecting a deformylation of said 3,5-dimethyl-4-hydroxybenzaldehyde to produce said 2,6-dimethylphenol at temperatures of 50 to 400° C. in the presence of a copper-containing catalyst system and a second solvent.

2. The process according to claim 1, wherein said first solvent is an alcohol having an alkyl group of from 1 to 6 carbon atoms.

3. The process according to claim 1, wherein said iron-containing catalyst system includes an iron-containing material and a carrier.

4. The process according to claim 3, wherein said iron-containing material is one selected from a group consisting of iron halide, iron oxide, iron sulfide, iron sulfate, iron carbonate, iron hydroxide, iron complex, iron ion, iron metal, organic iron compound and the combination thereof.

5. The process according to claim 4, wherein said iron-containing material is iron chloride.

6. The process according to claim 3, wherein said carrier of said iron-containing catalyst system is used for supporting said iron-containing material and is one selected from a group consisting of alumina, silica, titanium dioxide, zirconium dioxide, alumina-silica and zeolite.

7. The process according to claim 1, wherein said iron-containing catalyst system further includes a nitrogen-containing organic compound as promoter.

8. The process according to claim 7, wherein said nitrogen-containing organic compound is oxime.

9. The process according to claim 8, wherein said oxime is acetone oxime.

10. The process according to claim 1, wherein said second solvent is an alkane having an alkyl group of from 10 to 20 carbon atoms.

11. The process according to claim 1, wherein said copper-containing catalyst system includes a copper-containing material and a carrier.

12. The process according to claim 11, wherein said copper-containing material is one selected from a group consisting of copper halide, copper oxide, copper sulfide, copper sulfate, copper lactate, copper hydroxide, copper nitrate, copper oleate, copper phosphate, copper phosphoric, copper complex, copper ion, copper metal, organic copper compound and the combination thereof.

13. The process according to claim 12, wherein said copper-containing material is copper chloride.

14. The process according to claim 11, wherein said carrier of said copper-containing catalyst system is used for supporting the copper-containing material and selected from a group consisting of alumina, silica, titanium dioxide, zirconium dioxide, alumina-silica and zeolite.

15. A process of for preparing 2,6-dimethylphenol form 3,5-dimethyl-4-hydroxybenzaldehyde, comprising a step of:
    effecting deformylation of said 3,5-dimethyl-4-hydroxybenzaldehyde to produce 2,6-dimethylphenol at temperatures of 50 to 400° C. in the presence of a copper-containing catalyst system and a solvent.

* * * * *